(12) United States Patent
Makin et al.

(10) Patent No.: US 7,135,029 B2
(45) Date of Patent: Nov. 14, 2006

(54) ULTRASONIC SURGICAL INSTRUMENT FOR INTRACORPOREAL SONODYNAMIC THERAPY

(76) Inventors: Inder Raj S. Makin, 11377 Donwiddle Dr., Loveland, OH (US) 45140; Jurgen Mensch, Meertaarstraat 189, B-2430 Vorst-Laakdal (BE); Marcus Joannes Noppe, Pater Anonissemstraat 14, B-2920 Kalmthout (BE); Michael H. Slayton, 1323 E. Whalers Way, Tempe, AZ (US) 85283-2149

( * ) Notice: Subject to any disclaimer, the term of this patent is extended or adjusted under 35 U.S.C. 154(b) by 542 days.

(21) Appl. No.: 10/180,702

(22) Filed: Jun. 26, 2002

(65) Prior Publication Data
US 2003/0040698 A1 Feb. 27, 2003

Related U.S. Application Data
(60) Provisional application No. 60/302,070, filed on Jun. 29, 2001.

(51) Int. Cl.
*A61B 17/32* (2006.01)

(52) U.S. Cl. .................. 606/169; 606/167; 606/170; 606/171; 604/22; 604/103.01

(58) Field of Classification Search .............. 606/167, 606/171, 169, 170; 600/437, 471; 604/22, 604/19, 103.01, 103.02
See application file for complete search history.

(56) References Cited

U.S. PATENT DOCUMENTS

| | | | |
|---|---|---|---|
| 4,767,402 A | 8/1988 | Kost et al. | |
| 4,821,740 A | 4/1989 | Tachibana et al. | |

(Continued)

FOREIGN PATENT DOCUMENTS

| | | |
|---|---|---|
| RU | 2152773 C1 | 7/2000 |
| WO | 97/04832 A1 | 2/1997 |
| WO | 98/00194 A2 | 1/1998 |
| WO | 98/48711 A1 | 11/1998 |
| WO | 00/27293 A1 | 5/2000 |
| WO | 00/38580 A1 | 7/2000 |
| WO | 00/48518 A1 | 8/2000 |

OTHER PUBLICATIONS

Mitagotri et al., Determination of threshold energy dose for ultrasound induced transdermal drug transport, J. of controlled release, Jan. 2000.

Mitragotri S. et al., Transdermal drug delivery using low frequency sonophoresis, Pharmaceutical research, vol 13, 3, 1996.

(Continued)

*Primary Examiner*—Glenn K. Dawson
*Assistant Examiner*—Michael G. Mendoza

(57) ABSTRACT

The present invention relates, in general, to ultrasonic surgical instruments and, more particularly, to an intracorporeal ultrasonic surgical instrument for sonodynamic therapy. Disclosed is an ultrasonic surgical system comprising: a generator and an instrument comprising: a housing; a transducer; a semi-permeable membrane; a pharmaceutical agent; and an agent delivery system. The transducer is adapted to convert the electrical energy of the generator into mechanical energy. The pharmaceutical agent, delivered into a chamber of the semi-permeable membrane, is driven through the semi-permeable membrane by the mechanical energy. A method in accordance with the present invention comprises the steps of: providing a surgical instrument comprising: a housing; a transducer connected to the housing; a semi-permeable membrane; a pharmaceutical agent; and an agent delivery system; inserting the surgical instrument into a patient; delivering a drug to the patient; and locally activating the drug with the surgical instrument.

13 Claims, 9 Drawing Sheets

U.S. PATENT DOCUMENTS

| | | | |
|---|---|---|---|
| 5,007,438 A | * 4/1991 | Tachibana et al. | 607/152 |
| 5,016,615 A | 5/1991 | Driller et al. | |
| 5,190,766 A | * 3/1993 | Ishihara | 424/489 |
| 5,267,985 A | * 12/1993 | Shimada et al. | 604/290 |
| 5,275,166 A | 1/1994 | Vaitekunas et al. | |
| 5,449,370 A | 9/1995 | Vaitekunas et al. | |
| 5,617,851 A | 4/1997 | Lipkovker | |
| 5,630,420 A | 5/1997 | Vaitekunas | |
| 5,707,369 A | 1/1998 | Vaitekunas et al. | |
| 5,720,287 A | 2/1998 | Chapelon et al. | |
| 5,762,066 A | 6/1998 | Law et al. | |
| 5,800,392 A | * 9/1998 | Racchini | 604/103.01 |
| 5,807,306 A | * 9/1998 | Shapland et al. | 604/21 |
| 6,002,961 A | 12/1999 | Mitragotri et al. | |
| 6,113,558 A | 9/2000 | Rosenschein et al. | |
| 6,113,559 A | 9/2000 | Klopotek | |
| 6,113,570 A | 9/2000 | Siegel et al. | |
| 6,176,842 B1 | 1/2001 | Tachibana et al. | |
| 6,210,356 B1 | * 4/2001 | Anderson et al. | 604/22 |
| 6,595,989 B1 | * 7/2003 | Schaer | 606/41 |
| 6,685,648 B1 | * 2/2004 | Flaherty et al. | 600/464 |
| 6,689,086 B1 | * 2/2004 | Nita et al. | 604/22 |
| 2001/0027325 A1 | 10/2001 | Beaupre | |

OTHER PUBLICATIONS

Tachibana et al., Transdermal delivery of insulin by ultrasonic vibration, J. Pharm., 43, 270, 1991.

Tachibana et al., Prototype therapeutic ultrasound emitting catheter for accelerating thrombolysis, JUM 16,529–535, 1997.

Unger, E. C., et al., Acoustically active liposheres containing Paclitaxel, a new therapeutic contrast agent, Investigative Radiology, vol 33, 12, 1998.

Unger E. C., et al., Ultrasound enhances Gene Expression of Liposomal Transfection, Investigative Radiology, vol 32, No. 12, Dec. 1997.

* cited by examiner

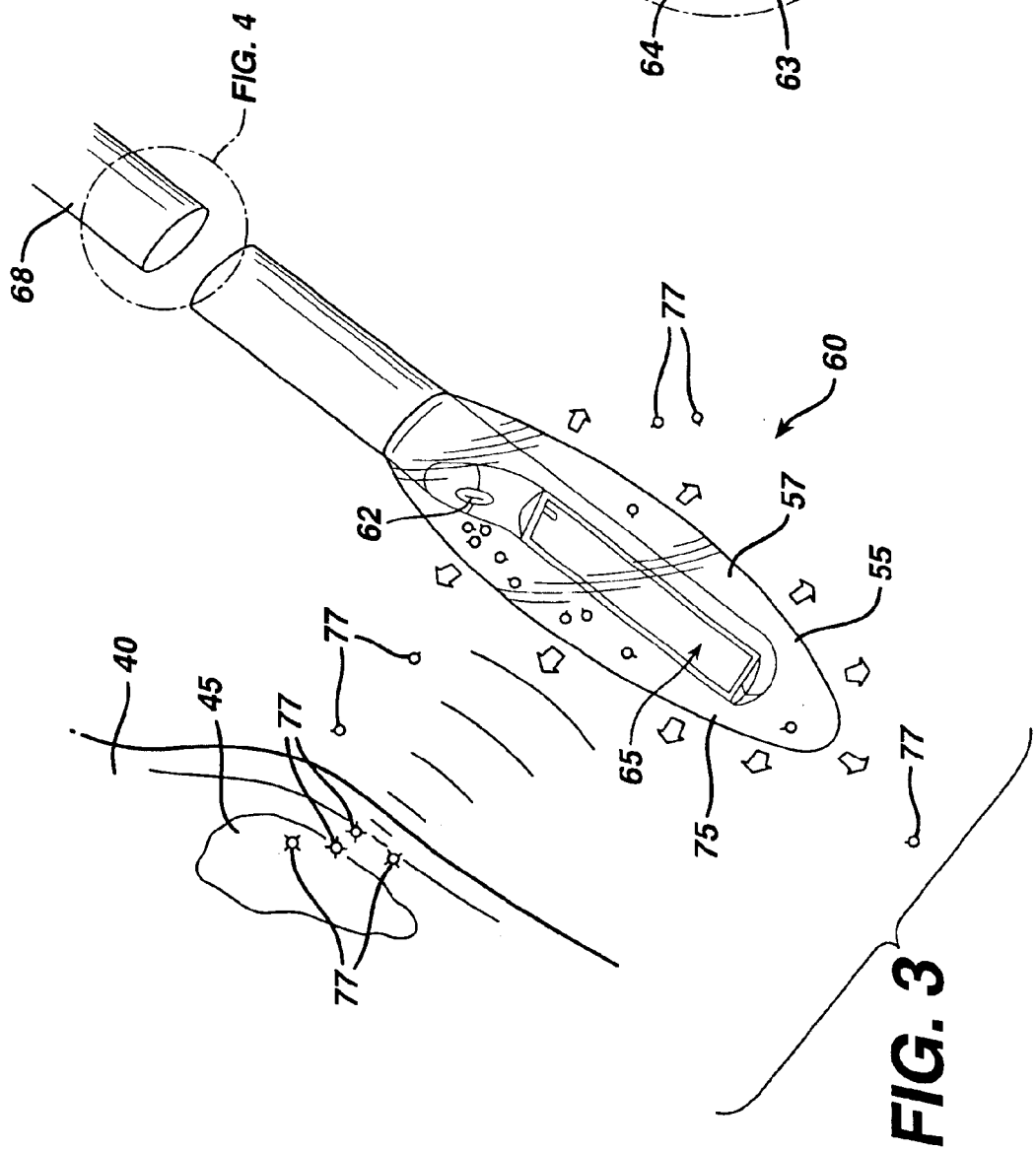
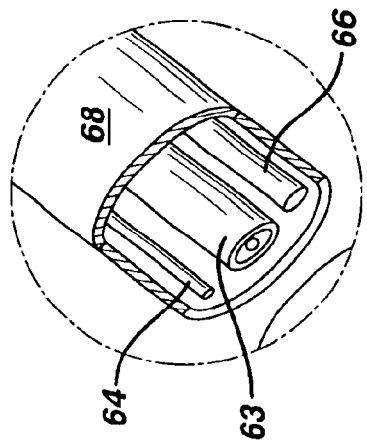
FIG. 3
FIG. 4

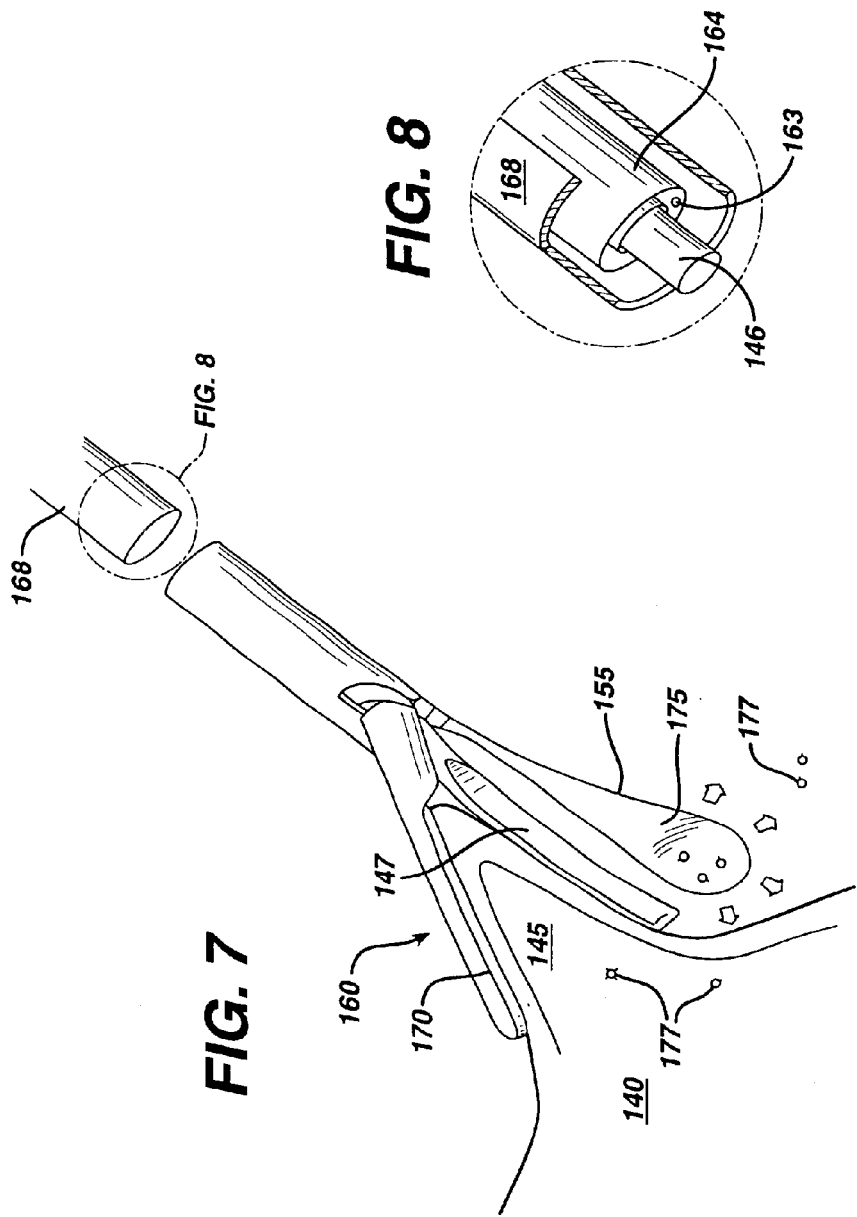

ULTRASONIC SURGICAL INSTRUMENT FOR INTRACORPOREAL SONODYNAMIC THERAPY

CROSS REFERENCE TO RELATED PATENT INFORMATION

This application is related to, and claims the benefit of, U.S. provisional patent application Ser. No. 60/302,070 filed Jun. 29, 2001, which is hereby incorporated by reference herein in its entirety.

FIELD OF THE INVENTION

The present invention relates, in general, to ultrasonic surgical instruments and, more particularly, to an ultrasonic surgical instrument for intracorporeal sonodynamic therapy.

BACKGROUND OF THE INVENTION

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy that may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Ultrasonic vibration is induced in the surgical end-effector by, for example, electrically exciting an electro-mechanical element, which may be constructed of one or more piezo-electric or magnetostrictive elements in the instrument handpiece. Vibrations generated by the electro-mechanical element are transmitted to the surgical end-effector via an ultrasonic waveguide extending from the transducer section to the surgical end-effector.

Another form of ultrasonic surgery is performed by High Intensity Focused Ultrasound, commonly referred to as "HIFU". HIFU is currently used for lithotripsy procedures where kidney stones are broken up into small pieces by ultrasonic shock waves generated through ultrasound energy focussed into the body from an extracorporeal source. HIFU is also under investigational use for treating ailments such as benign prostatic hyperplasia, uterine fibroids, liver lesions, and prostate cancer.

Examples of uses of ultrasound to treat the body can be found in U.S. Pat. Nos. 4,767,402; 4,821,740; 5,016,615; 6,113,570; 6,113,558; 6,002,961 6,176,842 B1; PCT International Publication numbers WO 00/27293; WO 98/00194; WO 97/04832; WO 00/48518; WO 00/38580; WO 98/48711; and Russian Patent number RU 2152773 C1.

Although the aforementioned devices and methods have proven successful, it would be advantageous to provide an intracorporeal instrument for sonodynamic therapy, and methods of sonodynamic treatment capable of improved outcomes for patients. This invention provides such an intracorporeal instrumennt and method for sonodynamic therapy.

SUMMARY OF THE INVENTION

The present invention relates, in general, to ultrasonic surgical instruments and, more particularly, to an ultrasonic surgical instrument for intracorporeal sonodynamic therapy. Specifically, the invention relates to an intracorporeal surgical instrument capable of enhanced/controlled delivery and activation of pharmaceutical agents as well as to achieve tissue ablation. Representative pharmaceutical agents include analgesics, anti-inflammatories, anti-cancer agents, bacteriostatics, neuro active agents, anticoagulants, high-molecular weight proteins, for example, for gene delivery, among others. The instrument is designed to operate in the kHz and/or MHz frequency ranges.

Disclosed is an ultrasonic surgical system comprising a generator and an instrument comprising a housing; a transducer connected to the housing; a depot for chemicals including a semi-permeable membrane, biodegradable packet, drug impregnated depots and liposomes among others; a pharmaceutical agent; and an agent delivery system. The generator is adapted to provide electrical energy to the transducer. The transducer is adapted to convert the electrical energy into mechanical energy. The agent delivery system delivers the pharmaceutical agent into a chamber of the semi-permeable membrane; and the pharmaceutical agent is driven through the semi-permeable membrane by the mechanical energy. Advantageously, the transducer may be combined with other surgical instruments such as ultrasound, iopntophoretic, laser, electrosurgical, for example RF, and eletroporative devices to achieve tissue ablation as well as the sonodynamic therapy.

The present invention has application in endoscopic and conventional open-surgical instrumentation as well as application in robotic-assisted surgery.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a perspective view of an ultrasonic surgical end-effector of an ultrasonic system in accordance with the present invention;

FIG. 4 is a sectioned view of a portion of an intense ultrasound instrument in accordance with the present invention;

FIG. 7 is a perspective view of an ultrasonic surgical instrument end-effector of an ultrasonic system in accordance with the present invention;

FIG. 8 is a sectioned view of a portion of an ultrasonic surgical instrument in accordance with the present invention;

DETAILED DESCRIPTION OF THE INVENTION

Figure 2:
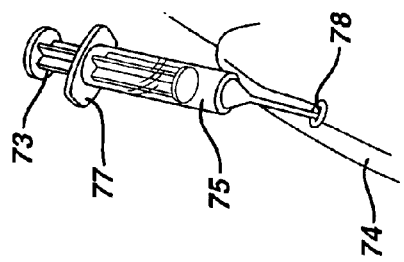
FIG. 2 is a perspective view of an alternate agent injection device for an ultrasonic instrument in accordance with the present invention.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is well known to those skilled in the art that ultrasound operating at kHz frequencies can reversibly change the permeability of cell barriers and/or activate drugs. Most of the work in this area describes the drug delivery applications through the skin, or enhancement of thrombolytic activity in the blood vessels. An approach where a surgeon performs an excision using an ultrasonic surgical instrument, and then "delivers" a chemotherapeutic agent in the treatment field would improve the treatment outcomes.

The attenuation coefficient for sound at kHz frequencies in tissue is very low, even assuming a radial spread of acoustic energy from the end effector. There is sufficient energy distal from the end effector, from a few millimeters to a couple of centimeters, such that the permeability of cells can be affected. Two examples, which are not intended to limit the scope of the invention, of intracorporeal drug delivery/enhancement are enabled by the present invention. One, local drug delivery in the region of surgical treatment as described earlier. Second, the therapeutic chemical agent is given intravenously, and the drug is activated in a region of interest during an interventional procedure using laparoscopic kHz and/or MHz frequency ultrasound.

For management of cancers, intra-operative delivery of chemotherapeutic agents and treatment with ultrasound energy is provided by the present invention to increase the efficacy of surgery and reduce recurrence rates, as well as to reduce the risk of seeding healthy sites with cancerous cells during intervention. Such local and site specific drug delivery approaches with kHz and/or MHz frequency ultrasound could be applied in surgical procedures, such as, for example, liver, colon, prostate, lung, kidney, and breast. A surgical patient may further benefit from the increase in treatment volume that may result from a chemical agent used in cooperation with kHz and/or MHz ultrasonic energy as well as from chemical agents used with the present invention that would otherwise be adversely affected if used with other forms of energy. In general, the chemical agents whose efficacy can be enhanced with the present invention may be chemotoxic drugs such as, for example, Paclitaxel, Docetaxel, trademark names of Bristol Meyers-Squibb or antibiotics, bacteriostatics, or cholinesterase inhibitors such as Galantamine, trademark name Reminyl of Johnson and Johnson, that may be delivered locally before completion of a surgical procedure. Chemical agents whose efficacy may be enhanced with the present invention further include local anesthetics such as, but not limited to, Novacaine, anti-inflammatories, corticosteroids, or opiate analgesics.

Figure 1:
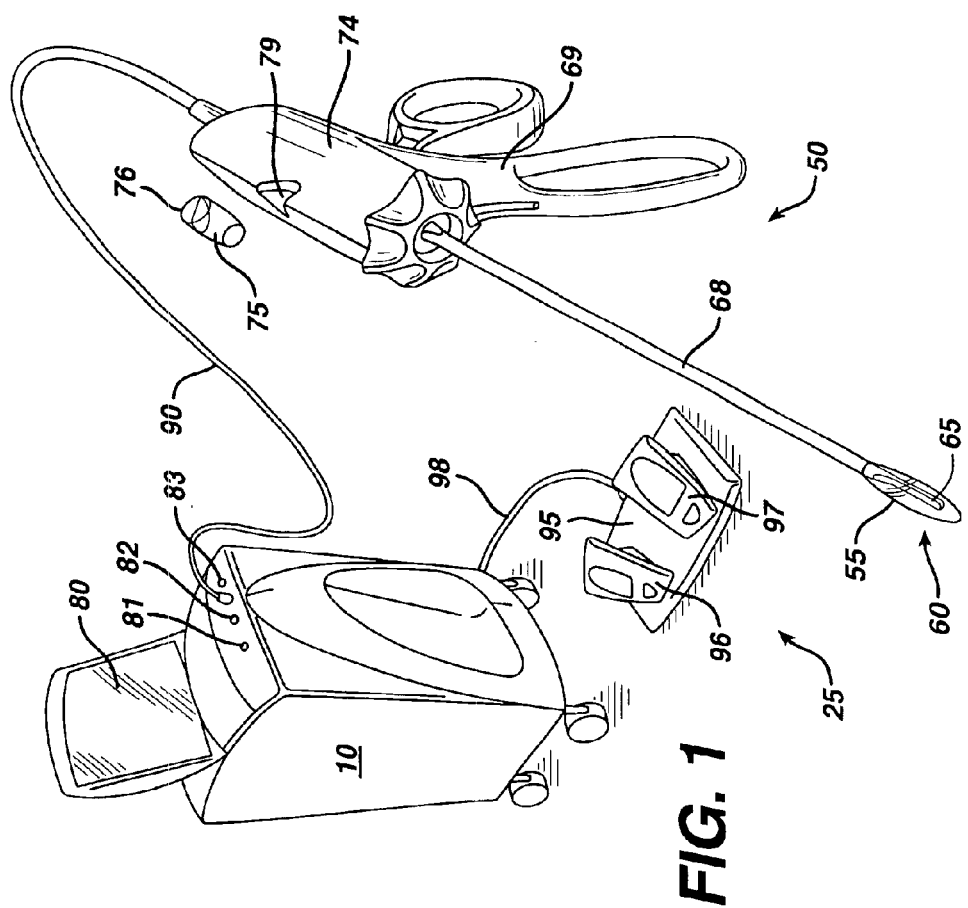
FIG. 1 is a perspective view of an ultrasonic system in accordance with the present invention.

FIG. 1 illustrates an ultrasonic system 25 for local delivery of an agent in combination with an intense ultrasound instrument 50 for activating or assisting transport of the agent. Intense ultrasound instrument 50 includes an elongated portion 68, a housing 74, a grip 69, a porous or semi-permeable membrane 55, and a port 79. An agent 75 is contained in a container 76 for insertion into port 79. Insertion of container 76 into port 79 may be done mechanically, or manually by the operator. Intense ultrasound instrument 50 includes a radiating end-effector 60. Intense ultrasound instrument 50 is connectable to a generator 10 via cable 90, that supplies electrical energy to radiating end-effector 60 for conversion by transducer 65 to ultrasonic stress waves. Radiating end-effector 60 comprises a plurality of embodiments including, but not limited to, single element, array-based end effectors, planar transducers, shaped transducers, or end effectors with active-passive element combinations.

A foot switch 95 is connected to generator 10 via cable 98 to control generator 10 function. A switch 96 and a switch 97 are included with foot switch 95 to control multiple functions. For example, switch 96 could provide a first level of energy to radiate end-effector 60 and a switch 97 could provide a second level of energy to radiate end-effector 60. Generator 10 may also include a display 80 for providing information to the user, and buttons or switches 81, 82, and 83 to allow user input into the generator such as, for example, turning the power on, setting levels, defining device attributes or the like.

FIG. 2 illustrates an alternate means of providing agent 75 to intense ultrasound instrument 50. In this embodiment, a syringe 77 contains agent 75 for injection to a surgical site within a patient. A plunger 73 may be depressed by the operator to deliver agent 75 to a surgical site via port 78.

FIG. 3 illustrates a method of using an instrument in accordance with the present invention. End-effector 60 is inserted into the body cavity of a patient, and located on or near tissue 40 that includes a spot or lesion 45 for treatment with agent 75. Spot or lesion 45 may be a cancerous region, a polyp, or other area that would benefit from treatment with agent 75. Semi-permeable membrane 55 contains agent 75 under instrument-off conditions, once agent 75 has been delivered to semi-permeable membrane 55. Agent 75 may be delivered to semi-permeable membrane 55 by way of an agent channel 63 (FIG. 4). An alternate embodiment of intense ultrasound instrument 50 contemplates the disposable use of intense ultrasound instrument 50 where semi-permeable membrane 55 is manufactured containing a preselected agent 75 located within semi-permeable membrane 55. The single use embodiment of intense ultrasound instrument 50 comprises disposal of intense ultrasound instrument 50, semi-permeable membrane 55, and/or end effector 60. Alternatively, and not by way of limitation of the invention, membrane 55 could take the form of a biocompatible biodegradable layer that is impregnated with a therapeutic chemical agent with or without the presence of cavitation nuclei. The therapeutic agent may be preferentially delivered at the target site when the ultrasound instrument 50 is energized.

When intense ultrasound instrument 50 is activated, agent 75 is driven through semi-permeable membrane 55, producing agent droplets 77. A suitable semi-permeable membrane 55 may be formed from, for example, nitrocellulose, tyvek, silicone, ethelyne vinyl acetate, or the like. Semi-permeable membrane 55 may be semi-permeable in specific regions and may be non-permeable in other regions to effectuate targeted release of the agent 75 through membrane 55. Further, semi-permeable membrane 55 may be biocompatible and have a tissue adhesive, allowing for the semi-permeable membrane 55 to be left within a body cavity, and/or may be adapted to dissolve within a body cavity. Agent droplets 77 are driven preferentially into tissue 40 by ultrasound energy, as shown below in ultrasound-mediated diffusion experiment results.

Intense ultrasound instrument 50 may further comprise the use of a suction system, an irrigation system, a snare, a viewing means, a coolant means, an imaging means, a biopsy system, a gene delivery means, and/or a number of cutting and/or coagulation means such as, for example, laser, iontophoretics, electroporative devices, or electrosurgical energy. The present invention further comprises the seeding of tissue 40 to facilitate enhanced ablation and/or agent droplet 77 delivery such as the introduction of foreign particles, the introduction of stabilized microbubbles, aeration, and/or a pulse profile designed to meet the needs of a particular medical application.

Agent 75 is injectable into chamber 57 of semi-permeable membrane 55 through port 62 under pressure from syringe 77, container 76, or by other suitable means of delivery. Agent 75 may be Vorozole, Paclitaxel, Docetaxel, bacteriostatics, antibiotics, anti-coagulants, glues, genes, chemotoxic agents, or any other agent having properties beneficial to the outcomes of the medical treatment or surgical procedure. Chemical agents whose efficacy may be enhanced with the present invention further include local anesthetics such as, but not limited to, Novacaine, anti-inflammatories, corticosteroids, or opiate analgesics.

FIG. 4 illustrates a section of elongated portion 68. Residing inside elongated portion 68 is an agent channel 63, a coaxial cable 66, and a lead 64. Agent channel 63 delivers the agent 75 from the proximal end of intense ultrasound instrument 50 to the radiating end-effector 60 via port 62. Coaxial cable 66 delivers electrical energy to transducer 65. In one embodiment, when electrically activated, transducer 65 operates preferably at 0.5–50 MHz, and more preferably at 0.5–10 MHz, and more preferably at 0.5–2 MHz. Lead 64 may be used to transmit a feedback signal from the radiating end-effector 60 to generator 10 such as, for example, temperature information from a thermocouple, acoustic noise level from a hydrophone, or the like. The present invention further contemplates the use of a plurality of coaxial cables 66, leads 64, and/or agent channels 63. Coaxial cable 66 may be designed from any conductive material suitable for use in surgical procedures. In one embodiment of the present invention, agent channel 63 comprises at least one lumen constructed from plastic, metal, rubber, or other material suitable for use in surgical procedures.

Figure 12:
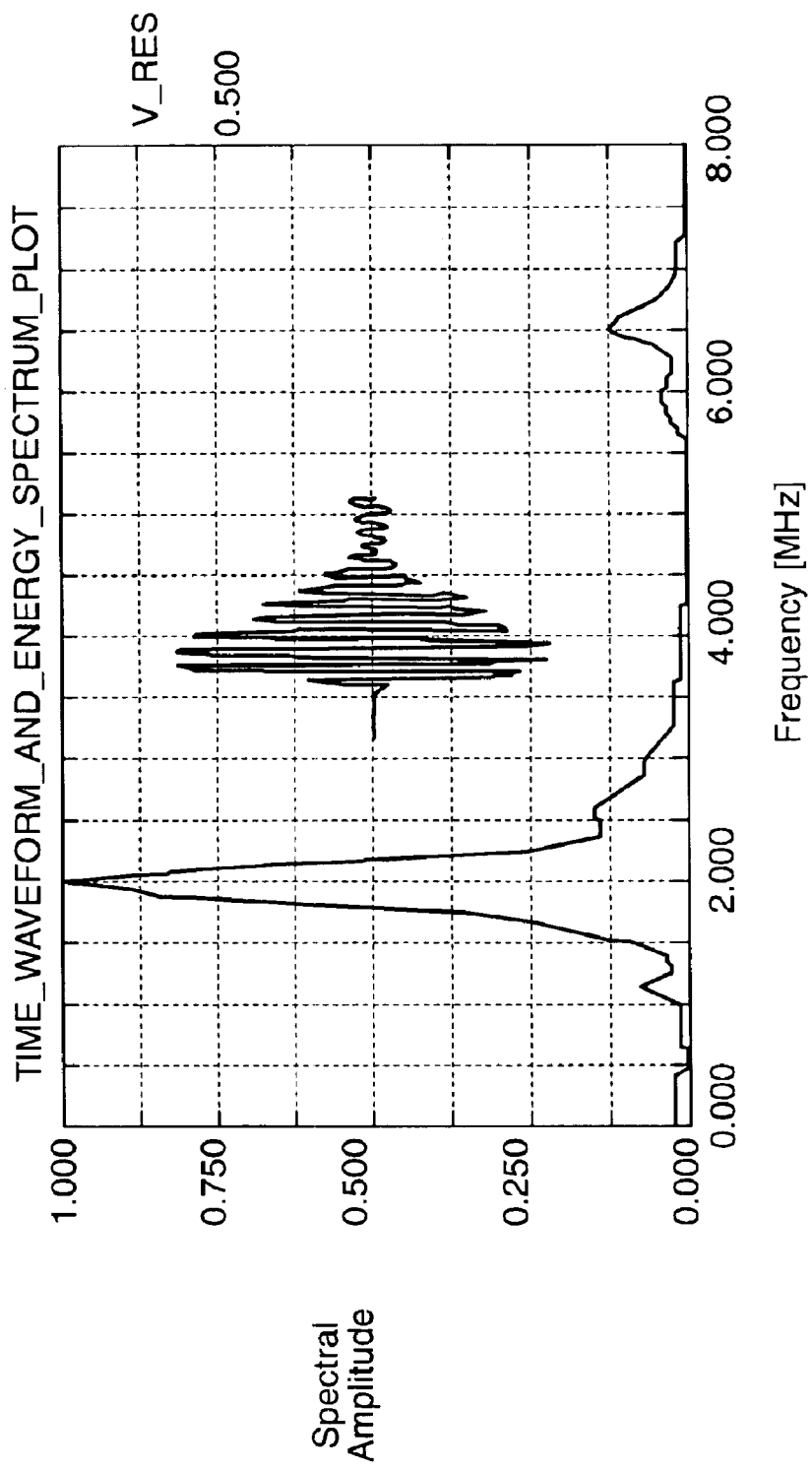
FIG. 12 is a graph of the response characteristics of a transducer in accordance with the invention of FIGS. 1–4.
Figure 13:
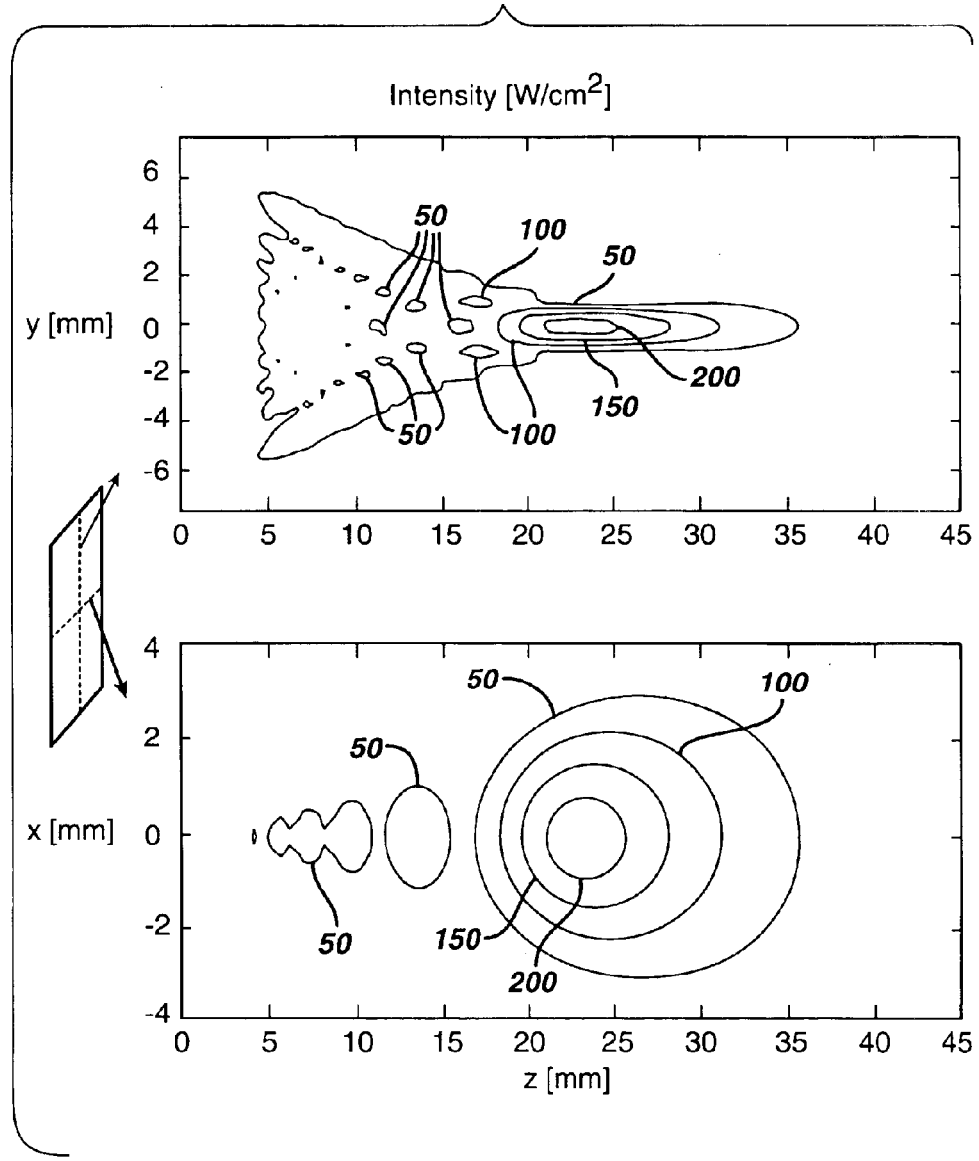
FIG. 13 is a plot of the calculated acoustic intensities of the transducer in accordance with the invention of FIGS. 1–4.

A design representative of an intra-corporeal MHz-frequency ablation and Sonodynamic therapy prototype may be, for example, a UTX Model #0008015 (UTX, Inc., Holmes, N.Y.). This may be designed around a 20 cm long tube that fits through a 5 mm trocar. At the distal end of this tube, there is one spherically curved ceramic element (4×15 mm, radius of curvature=25 mm). The transducer design accomplishes narrow bandwidth operation around 2 MHz. (as shown in FIG. 12). The acoustic output at source may be ~20W/cm$^2$. The acoustic intensity around the focal zone may be on the order of 200 W/cm$^2$, (FIG. 13), sufficient to cause tissue ablation in the treatment volume. In addition, there is sufficient acoustic energy range available for accomplishing enhanced drug-delivery or drug activation steps.

As is known in the art, the connecting cable 90 may be shielded coax. If needed, there may be an additional electrical matching network between the power amplifier and the transducer. The front faces of the transducer active surfaces have acoustic matching layers. The transducers are "air-backed." Thin, 0.125 mm, diameter thermocouples may be attached close to the ceramic faces that help monitor any self heating of the ultrasonic sources. Membrane 55 may be silicone, polyurethane, or polyester-based balloons to ensure that most of the energy radiated by the transducer is delivered to the tissue and not reflected back from the source tissue interface.

A further embodiment of ultrasonic system 25 comprises the systemic delivery of agent 75 in cooperation with intense ultrasound instrument 50. Agent 75 may be ingested, injected or systemically delivered by other suitable means. Intense ultrasound instrument 50 may then be activated on or near tissue 40 where the effects of intense ultrasound are desired.

Figure 6:
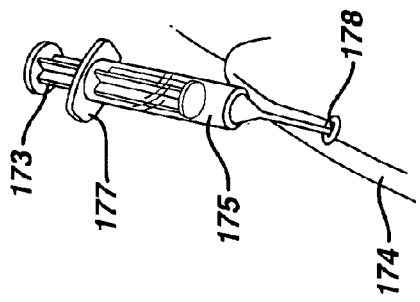
FIG. 6 is a perspective view of an alternate agent injection device for an alternate embodiment of an ultrasonic instrument in accordance with the present invention.
Figure 5:
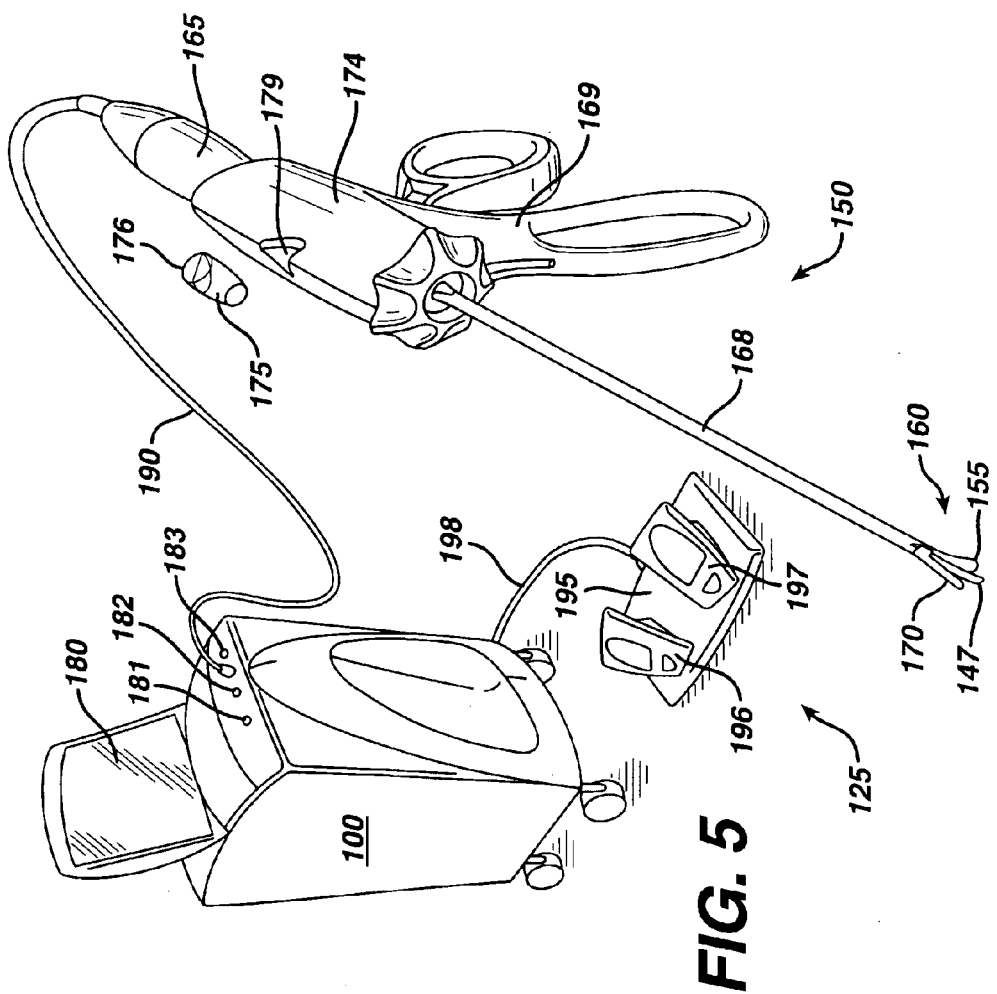
FIG. 5 is a perspective view of an alternate embodiment of an ultrasonic system in accordance with the present invention.
Figure 9:
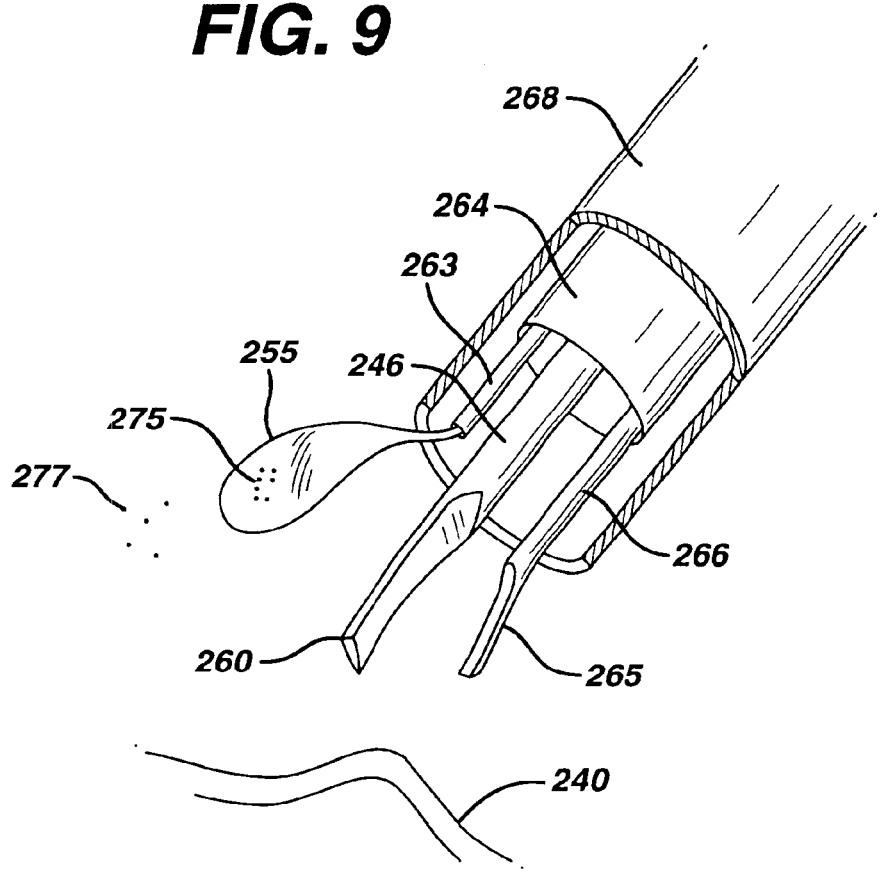
FIG. 9 is a sectioned view of a portion of an ultrasonic surgical instrument in accordance with the present invention.
Figure 10:
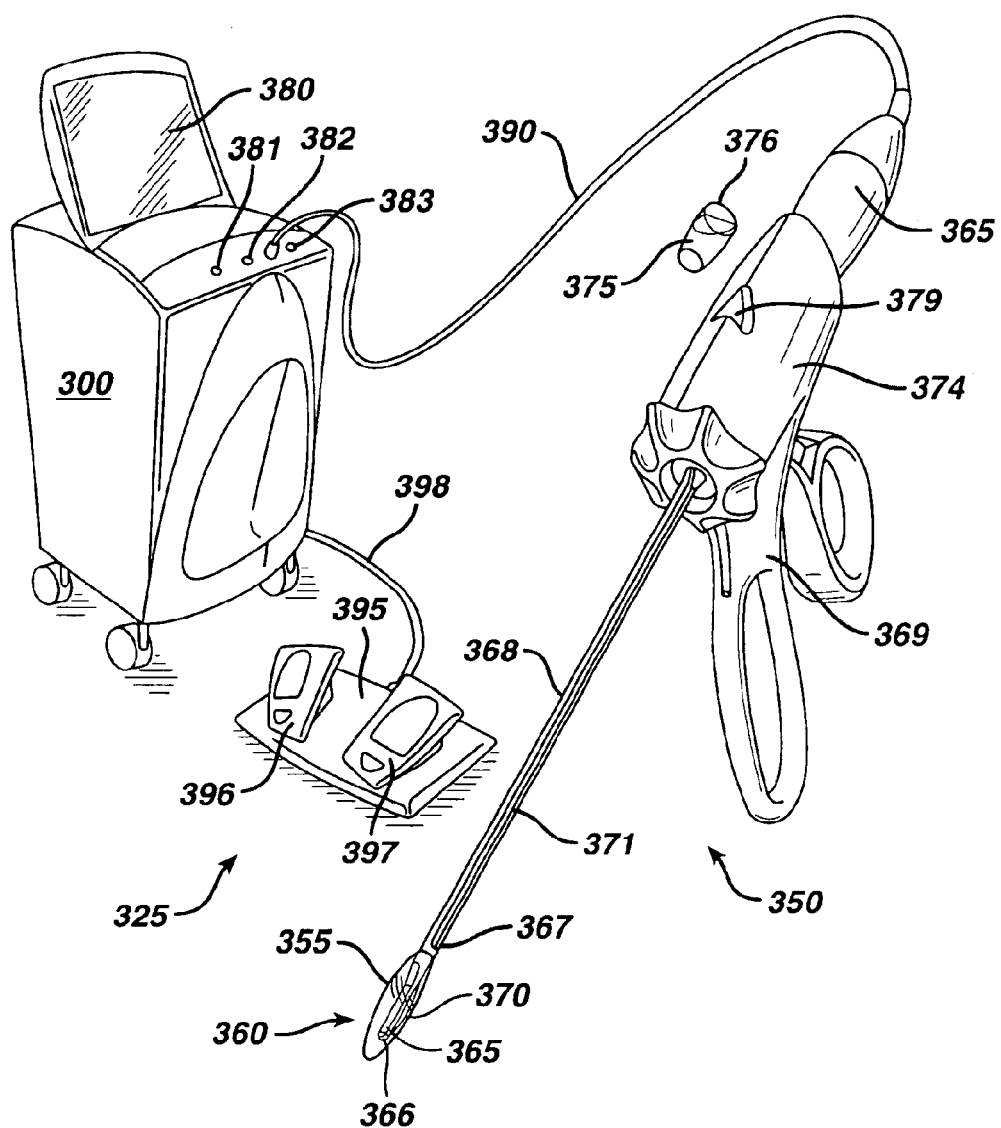
FIG. 10 is a perspective view of an alternate embodiment of an ultrasonic system in accordance with the present invention.

FIG. 5 illustrates an ultrasonic system 125 for local delivery of an agent 175 in combination with an ultrasonic surgical instrument 150 for activating or assisting transport of the agent 175. Ultrasonic surgical instrument 150 includes an elongated portion 168, a housing 174, an electro-mechanical element 165, for example, a piezoelectric transducer stack, a grip 169, a semi-permeable membrane 155, and a port 179. An agent 175 is contained in a container 176. Container 176 is insertable into port 179 of a housing 174. Alternatively, agent 175 may be delivered via a syringe 177 through a port 178 as shown in FIG. 6. Ultrasonic surgical instrument 150 includes a contact end-effector 160. Ultrasonic surgical instrument 150 is connectable to a generator 200 via cable 190, that supplies electrical energy to a transducer 165 that delivers stress waves to contact end-effector 160 via a waveguide 146 (FIG. 8). In one embodiment, when electrically active, electro-mechanical element 165 operates preferably at 10–200 kHz, more preferably and more preferably at 10–75 kHz. A clamp arm 170 may be attached to elongated portion 168, to provide compression of tissue 145 (FIG. 7) between clamp arm 170 and a blade 147 at the distal end of waveguide 146. Blade 147 comprises a plurality of embodiments including, but not limited to, a curved form, a straight form, a ball form, a hook form, a short form, a long form, or a wide form.

Referring now to FIG. 7 end-effector 160 may be inserted into the body cavity of a patient, and located on or near tissue 140 that includes a spot or lesion 145 for treatment with agent 175. Spot or lesion 145 may be a cancerous region, a polyp, or other area that would benefit from treatment with agent 175. Semi-permeable membrane 155 contains agent 175 under instrument-off conditions once agent 175 has been delivered to semi-permeable membrane 155. Agent 175 may be delivered to semi-permeable membrane 155 by way of an agent channel 163 (FIG. 8). An alternate embodiment of ultrasonic surgical instrument 150 comprises the single use of ultrasonic sugical instrument 150 where semi-permeable membrane 155 may be manufactured containing a pre-selected agent 175 located within semi-permeable membrane 155. The single use embodiment of ultrasonic surgical instrument 150 further contemplates disposal of ultrasonic surgical instrument 150, semi-permeable membrane 155, and/or end effector 160. When ultrasonic surgical instrument 150 is activated, agent 175 is driven through semi-permeable membrane 155, producing agent droplets 177. A suitable semi-permeable membrane 155 may be formed from, for example, nitrocellulose, tyvek, silicone, ethelyne vinyl acetate, or the like. Agent droplets 177 are then driven preferentially into tissue 140 by ultrasound energy, as shown below in ultrasound-mediated diffusion experiment results. Ultrasonic surgical instrument 150 further contemplates the use of a suction system, an irrigation system, a snare, a viewing means, and/or a number of cutting and/or coagulation means such as, for example, laser, iontophoretics, electroporative devices, or electrosurgical energy.

FIG. 8 illustrates a section of elongated portion 168. Residing inside elongated portion 168 may be an agent channel 163, solid waveguide 146, and a lead 164. Agent channel 163 delivers the agent 175 from the proximal end of ultrasonic surgical instrument 150 to the contact end-effector 160. Lead 164 may be used to transmit a signal from the radiating end-effector 160 to generator 200 such as, for example, temperature information from a thermocouple, acoustic noise level from a hydrophone, or the like. The present invention further contemplates the use of a plurality of leads 164 and/or agent channels 163. In one embodiment of the present invention, agent channel 163 comprises at least one lumen constructed from plastic, metal, rubber, or other material suitable for use in surgical procedures.

FIG. 9 illustrates an embodiment of the invention that combines the disclosures of FIGS. 1 and 5 and enables operation of a surgical instrument in both the KHz and MHz operating range. Shown is a section of elongated portion 268 of an overall system as shown in FIG. 5. Residing inside elongated portion 268 may be an agent channel 263, a transducer 265 in combination with a coaxial cable 266 for MHz operation, a solid waveguide 246 in combination with end effector 260 for KHz operation, and a lead 264. Agent channel 263 delivers the agent 275 from the proximal end of coupled ultrasound instrument 250 (not shown) to the semi-permeable membrane 255. Coaxial cable 266 delivers electrical energy to transducer 265. In one embodiment, when electrically activated, transducer 265 operates preferably at 0.5–50 MHz. Lead 264 may be used to transmit a signal from the distal end of coupled ultrasound instrument 250 to generator 10 such as, for example, temperature information from a thermocouple, acoustic noise level from a hydrophone, pulse-echo information from the target region, or the like. The present invention contemplates the use of a plurality of coaxial cables 266, leads 264, and/or agent channels 263. Coaxial cable 266 may be designed from any conductive material suitable for use in surgical procedures. In one embodiment of the present invention, agent channel 263 comprises at least one lumen constructed from plastic, metal, rubber, or other material suitable for use in surgical procedures.

The coupled ultrasonic instrument (not shown) comprises the use of an end effector 260 (kHz operation) connected to a waveguide 246 in cooperation with a transducer 265 (MHz) connected to a coaxial cable 266 and a semi-permeable membrane 255 connected to agent channel 263. Waveguide 246 may be coupled to an electro-mechanical element (not shown) located at the proximal end of the coupled ultrasonic instrument. In one embodiment of the present invention, the electro-mechanical element connected to waveguide 246 operates at 10–200 kHz. In one embodiment of the present invention, transducer 265 operates preferably at 0.5–50 MHz, and more preferably at 0.5–10 MHz. Accordingly, end effector 260 may be used simultaneously or alternately with transducer 265, or end effector 260 and transducer 265 may be used independently. The present invention comprises the method of using waveguide 246 with end effector 260 and/or transducer 265 to perform excision, hemostasis, ablation, and/or coagulative necrosis, prior to the delivery of agent 275 to semi-permeable membrane 255. Following necessary excision and hemostasis, agent 275 may be delivered through agent channel 263 into semi-permeable membrane 255, or agent 275 may be delivered systemically.

When transducer 265 and/or end effector 260 are activated, agent 275 is driven through semi-permeable membrane 255, producing agent droplets 277. A suitable semi-permeable membrane 255 may be formed from, for example, nitrocellulose, tyvek, silicone, ethelyne vinyl acetate, or the like. Agent droplets 277 are then driven preferentially into tissue 240 by ultrasound energy, as shown below in ultrasound mediated diffusion experiment results. The coupled ultrasonic instrument further comprises the use of a suction system, an irrigation system, a snare, a viewing means, and/or a number of cutting and/or coagulation means such as, for example, laser or electrosurgical energy. The waveguide 246 and associated end effector 260 may be used in cooperation with transducer 265 to facilitate a local (omnidirectional) tissue effect or a distant (focused) tissue effect depending on the needs of the application. The coupled ultrasound instrument further contemplates a transducer 265 surrounded by semi-permeable membrane 255, where agent channel 263 may be within or substantially near transducer 265 to facilitate the delivery of agent 275 into semi-permeable membrane 255 surrounding transducer 265. In a further embodiment of the present invention, semi-permeable membrane 255 may surround end effector 260, or may surround both end effector 260 and transducer 265.

FIG. 10 illustrates an ultrasonic system 325 for local delivery of an agent in combination with an intense ultrasound instrument 350 for activating or assisting transport of the agent 375 in combination with a first feedback device 366 and a second feedback device 367. Feedback devices 366 and 367 may be one or a plurality of piezo sensors, piezo receivers, thermocouples, non-thermal response monitors, thermal response monitors, cavitation monitors, streaming monitors, ultrasonic imaging devices, drug activation monitors, infusion rate controls, source controls, duty cycle controls, frequency controls, or other suitable means of monitoring and/or controlling a surgical procedure. Unless otherwise specified, all "300" series reference numerals have the same function as the corresponding reference numerals of FIG. 1, but it is evident that feedback devices 366 and 367 are useful in any of the embodiments of the invention presented herein.

In one embodiment of the present invention, first feedback device 366 is a piezo sensor attached to the distal portion of end effector 360, is coupled via wire 370 to a feedback monitor (not shown), in the form of a broad bandwidth pulser-receiver. Feedback device 366 in the form of a piezo sensor may be driven and controlled by the broad bandwidth pulser-receiver in order to acquire standard A-line (pulse echo) data from the region of interest, and to monitor morphological changes in the tissue 40. A further embodiment of the present invention comprises a feedback device 366 in the form of a piezo sensor used to estimate the temperature of the treatment volume using ultrasonic (remote) means, such as change in sound speed and/or the attenuation coefficient, and to facilitate monitored therapy. A further embodiment of the present invention contemplates feedback device 366 in the form of a piezo reciever to actively, and/or passively, monitor the cavitational activity in the therapy zone. Used in cooperation with a broad bandwidth pulser-receiver, this technique can be implemented by recording and processing the broad bandwidth acoustic emissions resulting from the bubble growth and collapse due the therapeutic ultrasound field in the region of treatment. Alternatively, the higher harmonic such as, for example, the $2^{nd}$ or $3^{rd}$, or the sub-harmonic response due to the high-power field in the therapeutic zone can be recorded and correlated to the tissue therapy, or to estimate the amount of agent 75 activated. Further, the streaming field resulting from the therapy acoustic field may be monitored using Doppler flow techniques. The strength of the flow signal may be correlated to the magnitude of advection, or delivery of agent 75, within the treatment volume.

A second feedback device 367 may be a thermocouple attached to the elongated portion 368 comprising at least one wire 371, where at least one wire 371 is attached to both second feedback device 367 and to a feedback monitor (not shown). Feedback monitor (not shown) may be for example, a broad bandwidth pulser-receiver, or other suitable means of monitoring and/or controlling a surgical procedure. Wire 371 may be constructed from silver, stainless steel, or other conductive material suitable for use in surgical procedures. Second feedback device 367 may be located at any point along elongated portion 368 depending on the needs of a particular medical application. In one embodiment of the present invention, feedback device 367 may be a thermocouple attached to elongated portion 368, where the feedback device 367, in the form of a thermocouple, monitors the region of interest during ablation and/or drug activation phases.

The present invention contemplates one or a plurality of feedback devices 366 and/or feedback devices 367 used within a system feedback loop to control, for example, the therapy source, pulsing, treatment time, and/or rate of drug infusion, in order to optimize the ablative and drug activation-based treatments.

Protocol for Ultrasound-mediated Diffusion Experiments

A method for treating tissue in accordance with the present invention comprises the steps of: providing a surgical instrument, the instrument comprising: a housing; a transducer connected to the housing; a semi-permeable membrane surrounding the transducer; a pharmaceutical agent; and an agent delivery system; inserting the surgical instrument into a body cavity of a patient; delivering a drug to the patient; and locally activating the drug with the surgical instrument. For purposes herein, locally is defined as within a range of about 0.5 mm to 50 mm from the end-effector of the instrument. Other steps in accordance with the present invention include achieving hemostasis, excising tissue, coagulating tissue, and cutting tissue.

Experiments were performed to determine if the present invention could transport a chemical agent of interest to a potential therapeutic site. An appropriate agent, Vorozole, a model chemical agent from Janssen Pharmaceutica in Belgium was selected as a chemical drug for permeation through biological barriers.

The representative 20 kHz and 1 MHz sources are described as follows. The 20 kHz sonicator system is available from Cole Parmer, Inc., Vernon Hills, Ill.—Ultrasonic Homogenizer, Model CPX 400. The 1 MHz source was a custom designed transducer available from UTX, Inc., Holmes, N.Y. (e.g., UTX Model #9908039). A suitable acoustic power output ranges from 1–10W, pulsed at 5–75% duty cycle. A suitable source geometry ranges from 1–5 MHz, flat geometry (19 mm diameter ceramic disks (preferably PZT-4)). Transducers should be designed for high-power long-term operation (up to 26 hours), air or Corporene-backed (narrow bandwidth tuning), high-temperature epoxy front face matching. Embedded thermocouples in close proximity of the ceramic may provide feedback for the source surface temperature. A number of source cooling schemes may be implemented (for example, transducer housing with a water jacket, or circulating water at the front face of transducer, separated from the drug reservoir by using polymer-based membranes or stainless steel shim stock). The cable for the transducers may be double-shielded coax, teflon coated (high-temperature), or gold braided thin-gauge cable.

For active diffusion experiments with Vorozole, 16 ml of 5% HP-β-CD with 0.05% $NaN_3$ in water was added into the receptor compartment of glass diffusion cells. A Teflon-coated magnetic stirring bar was also added in the receptor compartment. The Franz cells were then placed on top of a stirring plate set at about 600 rpm.

To perform the ultrasound-mediated experiments, a 20 kHz and a 1 MHz probe were mounted in the donor compartment close to the skin surface. The formulations were added until the probes were immersed in the liquid and ultrasound sources were turned on.

The power setting indicated on the 20 kHz system relates to a correspondingly increased acoustic field radiated from the horn tip. The acoustic power radiated by the MHz frequency transducers was nominally ~4 W for the voltage used in our study at 1 MHz. In addition, the acoustic intensity over time ($I_{temporal}$) was a function of the pulsing regime used for a given experiment.

The experiments were conducted over 20 hours. Samples were collected in the following successive order: 1, 2, 3, 4, 5, 6, 7, 8, 10, 12, 14, 16, 20 hours.

After the incubation period, the receptor fluid was collected and stored at 4° C. until HPLC analysis was performed. The formulation was removed from the donor side with a syringe and Kleenex tissues. The diffusion cells were dismantled and the skin was carefully removed. The surface was cleaned consecutively with a dry Kleenex tissue, an ethanol-wetted tissue and a dry tissue. The skin was evaluated for morphologic changes due to the exposure to ultrasound.

Figure 11:
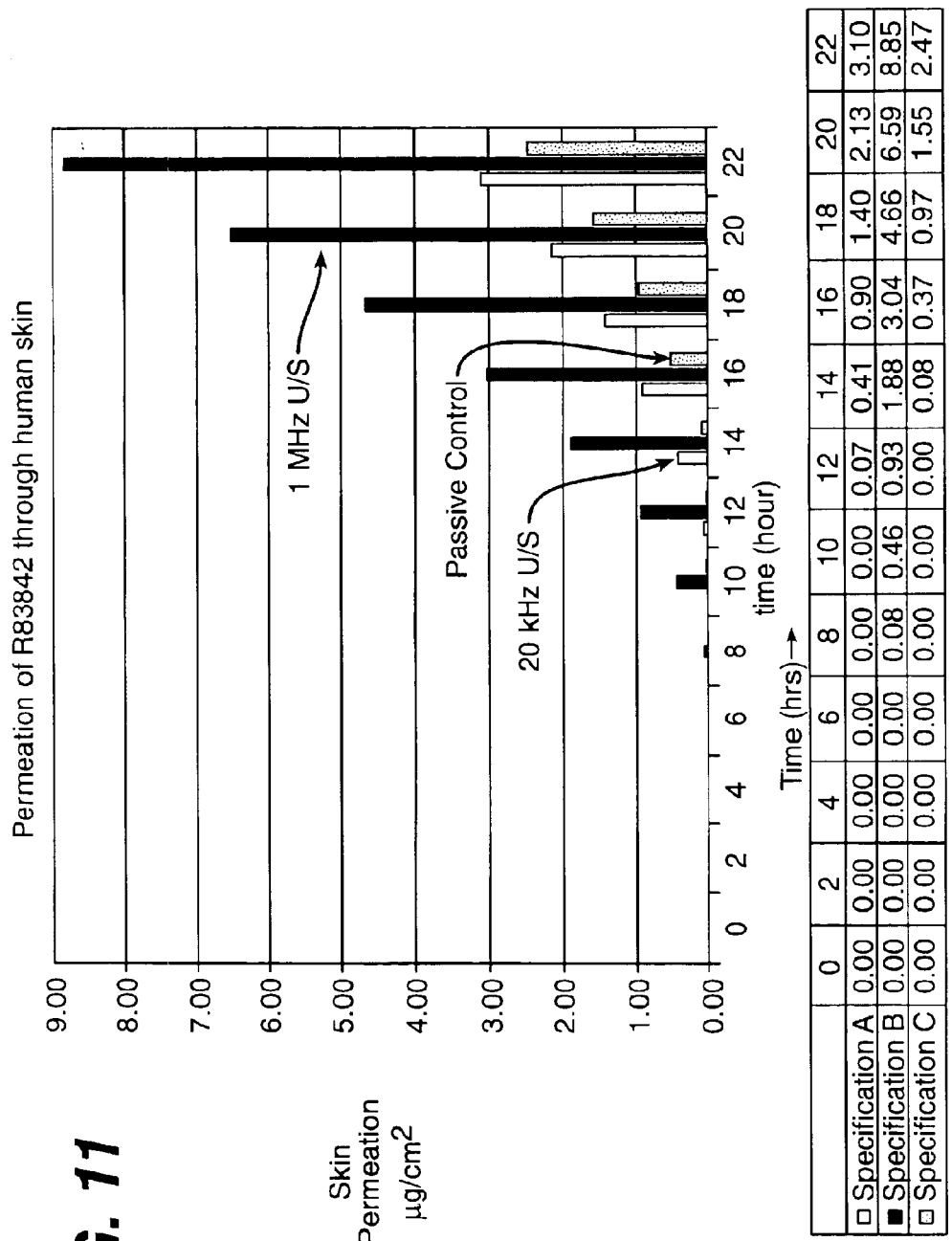
FIG. 11 is a graph illustrating the transport of an agent with and without ultrasound energy.

Parallel experiments for passive diffusion of the drug were conducted whereby the set-up was identical for ultrasound exposure to the tissue, except that the skin was not exposed to any ultrasound energy. The result of the above experiment is illustrated in FIG. 11, illustrating that an ultrasonic surgical instrument 50 increases the transport of Vorozol through tissue. Specification A is 20 kilohertz ultrasound with a tip displacement of approximately 10 micrometers peak-to-peak, 0.5 Seconds on, 12.5% duty cycle. Specification B is 1 Megaherts ultrasound at approximately 4 Watts power, 4 seconds on at 50% duty cycle. Specification C is passive permeation.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. An ultrasonic surgical system comprising:
a housing;
a tubular sheath having a proximal end connected to the housing and a distal end, the tubular sheath defining a longitudinal axis;
a transducer extending distally of the distal end of the tubular sheath;
a membrane extending distally of the distal end of the tubular sheath and having a hollow volume for receiving a pharmaceutical agent and the transducer; and
a pharmaceutical agent delivery system.

2. The ultrasonic surgical system of claim 1, wherein said transducer operates within the range of about 500 kilohertz to about 50 megahertz.

3. The ultrasonic surgical system of claim 2, wherein said transducer operates within the range of about 500 kilohertz to about 2 megahertz.

4. The ultrasonic surgical system of claim 3, wherein said membrane is porous or semi-permeable.

5. The ultrasonic surgical system of claim 1, further comprising a feedback device selected from the group consisting of a non-thermal response monitor, a thermal response monitor, a cavitation monitor, a streaming monitor, an ultrasonic imaging device, a drug activation monitor, an infusion rate control, a source control, a duty cycle control, a piezo sensor, a piezo receiver, a thermocouple, and a frequency control.

6. An ultrasonic instrument comprising:
a housing:
a tubular sheath having a proximal end connected to the housing and a distal end, the tubular sheath defining a longitudinal axis;
a ultrasonic transducer extending distally of the distal end of the tubular sheath;
a membrane having a hollow volume for receiving a pharmaceutical agent and the transducer; and
a pharmaceutical agent delivery system;
wherein said pharmaceutical agent delivery system delivers said pharmaceutical agent into the hollow volume of said membrane; and
whereby said pharmaceutical agent is driven through said membrane by ultrasonic energy delivered from said transducer.

7. An ultrasonic surgical system comprising:
a) a generator;
b) an instrument comprising:
i) a housing;
ii) a transducer assembly carried by the housing and adapted to vibrate at an ultrasonic frequency;
iii) a waveguide having a first end adapted to receive ultrasonic vibration from the transducer assembly and a second end operatively connected to an end-effector;
iv) a membrane surrounding said end-effector;
v) a pharmaceutical agent contained in the membrane;
wherein said generator is adapted to provide electrical energy to said transducer assembly;
wherein said transducer is adapted to convert said electrical energy into ultrasonic vibration; and
whereby said pharmaceutical agent is driven through said membrane by said ultrasonic vibration.

8. The ultrasonic surgical system of claim 7, wherein said transducer assembly operates within the range of about 10 kilohertz to about 200 kilohertz.

9. The ultrasonic surgical system of claim 7, wherein said membrane is porous or semi-permeable.

10. An ultrasonic surgical instrument comprising:
a) a housing;
b) a tubular sheath having a proximal end connected to the housing and a distal end, the tubular sheath defining a longitudinal axis;
c) a transducer extending distally of the distal end of the tubular sheath;
c) a membrane extending distally of the distal end of the tubular sheath and having a hollow volume for receiving a pharmaceutical agent and, the membrane located external and adjacent said transducer; and
d) a pharmaceutical agent.

11. The ultrasonic surgical system of claim 10, wherein said transducer operates within the range of about 500 kilohertz to about 50 megahertz.

12. The ultrasonic surgical system of claim 10, wherein said transducer operates within the range of about 10 kilohertz to about 200 kilohertz.

13. The ultrasonic surgical system of claim 10, wherein said membrane is porous or semi-permeable.

* * * * *